(12) United States Patent
Lenglet et al.

(10) Patent No.: US 6,488,839 B1
(45) Date of Patent: Dec. 3, 2002

(54) PROCESS AND FURNACE FOR STEAM-CRACKING A FEEDSTOCK THAT CONTAINS ETHANE AND/OR PROPANE

(75) Inventors: Eric Lenglet, Sainte Foy les Lyons (FR); Christian Busson, Charbonniere (FR); Luc Nougier, Sainte Foy les Lyons (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/568,050

(22) Filed: May 10, 2000

(30) Foreign Application Priority Data

May 11, 1999 (FR) .............................................. 99 06190

(51) Int. Cl.$^7$ .............................. C10G 9/36; C07C 4/04
(52) U.S. Cl. ...................... 208/130; 585/648; 585/650; 585/652; 585/925
(58) Field of Search ......................... 208/130; 585/648, 585/650, 652, 925

(56) References Cited

U.S. PATENT DOCUMENTS

| | | | |
|---|---|---|---|
| 4,762,958 A | | 8/1988 | Martens et al. .............. 585/613 |
| 4,997,525 A | * | 3/1991 | Martens et al. .............. 196/110 |
| 5,124,003 A | * | 6/1992 | Martens et al. .............. 196/110 |
| 6,271,431 B1 | * | 8/2001 | Busson et al. .............. 208/130 |

FOREIGN PATENT DOCUMENTS

| | | |
|---|---|---|
| FR | 2.032.437 | 11/1970 |
| FR | 2760465 | 9/1998 |

* cited by examiner

Primary Examiner—Walter D. Griffin
(74) Attorney, Agent, or Firm—Millen, White, Zelano & Branigan, P.C.

(57) ABSTRACT

A steam-cracking process with a very high degree of severity of a feedstock that comprises at least 20% by weight of hydrocarbons of the group that is formed by ethane and propane in which the feedstock that is diluted with water vapor is circulated in the radiation zone of a furnace, in at least one pipe with a length L≧14 m and a hydraulic diameter that is greater than or equal to 34 mm in the end portion of the pipe at least, is described under the following conditions of dwell time τ and furnace output temperature COT:

120 ms≦τ≦2800 ms and 858° C.≦COT≦1025° C. to obtain a conversion of at least 77% of ethane of the feedstock if the feedstock contains ethane and/or a conversion of at least 96% of the propane of the feedstock if the feedstock contains propane, and to maintain this conversion for a cycle time that is greater than or equal to about 8 days.

39 Claims, 1 Drawing Sheet

PROCESS AND FURNACE FOR STEAM-CRACKING A FEEDSTOCK THAT CONTAINS ETHANE AND/OR PROPANE

The object of the invention is to carry out a steam-cracking of light feedstocks under very severe conditions and at a very high conversion level, in particular for feedstocks that are high in ethane or in a $C_2/C_3$ mixture.

Typically, these feedstocks contain at least 20% by weight of ethane and/or propane and at least 80% by weight of hydrocarbons with 2 and/or 3 carbon atoms. Most generally, these are mixtures of ethane and propane, which can also comprise variable amounts of propylene, as well as small amounts of ethylene, methane and hydrocarbons with 4 carbon atoms or more.

The steam-cracking of light feedstocks is a process that is extensively described in technical literature, for example in the work that is well known in the steam-cracking industry: "ETHYLENE KEYSTONE TO THE PETRO-CHEMICAL INDUSTRY" Ludwig Kniel, Olaf Winter, Karl Stork, Editor MARCEL DEKKER, INC., New York, 1980, (Reference 1).

The technological background is described in, for example, patents U.S. Pat. No. 4,762,958, FR-A 2 032 437 and FR-A 2 760 465.

Ethane, and to a lesser extent propane, is a feedstock that is fairly refractory for which it is difficult to obtain high conversion levels. The high conversion levels require very rigorous operating conditions of furnaces that result in high coking speeds that increase the skin temperatures of pyrolysis tubes and reduce the cycle times. The work that is cited provides ethane steam-cracking yields, page 65, at 50% and 60% of conversion, value typically used in steam-cracking furnaces. It is indicated on page 112 of this work that a conversion of 70% is beyond industrial possibilities with the technologies that are known at this time. The cracking furnaces actually comprise tubes or coils for circulating a gas mixture that contains water vapor, ethane and products that are obtained from cracking. These tubes are made of refractory alloys that are high in chromium, nickel and iron, such as the "HK40" alloy that is well known to one skilled in the art and that consists mainly of 25% chromium, 20% nickel and a balance of iron (aside from minor additions).

These alloys are limited in their operating conditions by metallurgic constraints, which limits the conversion of ethane and/or propane.

This does not mean that it is impossible for a given furnace to exceed nominal conversion, for example 60%, but if the heating of the burners is advanced to increase this conversion, it will not be possible to avoid an accelerated aging of the tubes and ruptures of the tubes, in particular by creep and carburation. The cycle times are also reduced very significantly because of a drastic increase of coking under very severe conditions required for high conversion levels of ethane and/or propane.

The manufacturers of pyrolysis tubes have made significant progress, however, and have developed refractory alloys that are higher-performing than the HK40: In particular the 25/35 alloys (Cr, Ni) with a balance of Fe plus some additions (Si, Mn, Nb, Ti . . . ), for example the "HP MOD" alloys, are known. More recently, 35/45 alloys (Cr, Ni) and even alloys with 40 or 45% of chromium, which contain less than 15% of iron, with a balance of nickel, aside from minor additions including 1 to 2.5% of silicon, were developed.

A list of materials for pyrolysis tubes, with their recommended use-limit compositions and temperatures is provided in "Proceedings of the 10th Ethylene Producers Conference" (1998) published by AIChE (Reference 2) in the article "Coke Reduction and Coil Life Extension," pp. 107–108 (Reference 2A).

With the highest-performing materials, the practicable conversion of ethane industrially has been brought to about 65%.

The thermal fluxes that are used in the cracking zone with radiation are variable according to the types of furnaces but between 50 and 120 $KW/m^2$, if they are related to the outside surface of the tubes. It is possible in particular to refer to the work of Reference 1, page 131, which mentions fluxes between 50 and 80 $KW/m^2$. It is also possible to refer to the work: "PROCEDES DE PETROCHIMIE [PROCESSES OF PETROCHEMISTRY]," Vol. 1, TECHNIP Editions, Paris, 1985 of A. Chauvel, G. Lefebvre, L. Castex (Reference 3), page 159, which mentions the mean fluxes between 75.5 and 104.5 $KW/m^2$.

Flow values of 50 KW correspond to the use of old HK40-type alloys, which are no longer used for the hottest end portion of the pyrolysis coils. With modern alloys, the fluxes that are used are typically between 80 and 120 KW. A correspondence between the flux and the maximum skin temperatures of the tubes is given in Reference 3, page 160.

Obviously, the tendency of the steam-cracking industry is to increase the thermal fluxes, by taking advantage of the better alloys that are available, to increase productivity as well as the level of severity of the steam-cracking (i.e., the conversion in the case of ethane).

Whereby the advances of the alloys are not without limit, it is difficult today, however, to exceed approximately 65% of conversion for ethane.

The metallurgists have therefore turned, in the most recent state of the art, to new improvements, in other directions:

Thus, two publications:
"A Low Coking Environment for Pyrolysis Furnaces—CoatAlloy—, M. Bergeron, E. Makarajh, T. McCall," and "Results of a Furnace Tube Surface Treatment in a Full Furnace Trial, D. Mullenix, A. Kurlekar"
were presented in the conference: "1999, AIChE Spring National Meeting, Eleven Annual Ethylene Producers Conference Mar. 16, 1999 HOUSTON, Tex." (Reference 4).

In these publications, recent (1998) industrial results of ethane steam-cracking with pyrolysis tubes comprising anti-coking surface coatings are presented. According to these publications, the limitation of coking makes it possible to increase the thermal fluxes and the conversion and to operate in a satisfactory manner (cycle time, behavior of materials) at a conversion of 70%. It was also proposed to use tubes that comprise a welded inside fin, in particular a helicoidal one, which has the effect of increasing the thermal transfer, and therefore the performances of the furnaces that use this technique.

To exceed this maximum conversion limit, developments have also been undertaken to use ceramic pyrolysis tubes or pipes. The operating temperatures of the ceramics are extremely high, and these materials completely eliminate the catalytic coking. A plan for a furnace with ceramic pyrolysis tubes for high-conversion ethane cracking was thus presented by one of the major engineering firms that build steam-cracking devices (Reference 2, article "Coke-free Cracking—Is It Possible" by Khoi (Paul) X Pham, Dennis Duncan, Joseph M. Gondolfe (Reference 2B), pp. 127–150).

In this article, it is shown that cycle times of at least 7 days were obtained with a ceramic tube for an ethane conversion of 75% (p. 139). It is indicated that the metallic tube of the same geometry led to clogging within 3 hours. The dwell times used are very short (less than 50 milliseconds (ms)), which is in accordance with the philosophy and the evolution of the steam-cracking industry for several decades.

The ethane conversions at 77% and more thus are not currently being envisioned and considered as possible within the scope of an industrial operation except with very particular and complex furnace designs that use ceramic materials.

The orientations of the steam-cracking industry of light feedstocks for the preferred production of ethylene are thus:

Use of the highest-performing refractory alloys and, moreover, ceramic materials.

Use of the highest acceptable thermal fluxes.

Use of the shortest possible dwell times (in particular less than or equal to 100 milliseconds).

The invention has as its object a steam-cracking process that makes it possible to crack the ethane and light feedstocks with conversions that are greater than or equal to 77% and even 80% or even greater than 95%. This process makes it possible not only to be able to carry out these conversions on a pilot laboratory furnace or on an industrial furnace on a temporary basis, but on industrial furnaces with operating conditions that are compatible with the requirements of the industry (service life of the tubes, cycle times, etc. . . . ).

Surprisingly and contrary to prior teaching, it was discovered that it is possible to obtain very high conversion levels mentioned above by using a steam-cracking process under very severe conditions of a feedstock that comprises at least 80% by weight of hydrocarbons that have 2 to 4 carbon atoms, and at least 20% by weight of hydrocarbons of the group of ethane and propane that is characterized in that:

The feedstock that is diluted with water vapor in a radiation zone of a furnace is circulated in at least one pipe with length $L \geq 16$ m and a hydraulic diameter that is greater than or equal to 34 mm in the end portion of the pipe at least, under the following conditions of dwell time $\tau$ and furnace output temperature COT:

$$150 \text{ ms} \leq \tau \leq 2800 \text{ ms};$$

$$858° \text{ C.} \leq COT \leq 1025° \text{ C.},$$

whereby the ratio of L/mean hydraulic diameter $D_H$, and dwell time $\tau$ is large enough to obtain at least one of the following results:

A conversion of at least 77% of the ethane of the feedstock, if the feedstock contains ethane.

A conversion of at least 96% of the propane of the feedstock, if the feedstock contains propane, whereby thermal flux $\emptyset$ in the radiation zone is low enough so that parameter $\xi 1$ that is defined by:

$$\xi 1 = \frac{[\emptyset^*]^2}{R}$$

with:

$$R = L/D_H, \quad \emptyset^* = \emptyset \times F$$

where $\emptyset$ is the mean thermal flux that is sent into the pipe in the radiation zone, in KW per m² of outside surface of the pipe, and F=

→0.85 if the end portion of the pipe comprises at least one inside fin or an anti-coking coating on at least one portion of its inside surface, →0.72 if the end portion of the pipe comprises at least one inside fin and an anti-coking coating on at least one portion of its inside surface, →1 otherwise, confirms $\xi 1 \leq 11$, whereby the value of $\xi 1$ is low enough to maintain this conversion for a cycle time that is greater than or equal to about 8 days, in particular at least 10 days, in particular at least 15 days, more particularly at least 20 days and typically at least 30 days.

Conventionally, for the definition of dwell time $\tau$, only a portion of the radiation zone in which the feedstock reached or exceeded the conventional temperature at the very beginning of steam-cracking of 650° C. is considered. The retention time is therefore conventionally the dwell time between the point where the temperature reaches 650° C. (or the input of the radiation zone if the input temperature is greater than 650° C.) and the starting point of quenching of cracked gases at the output of the radiation zone of the furnace. This dwell time therefore comprises the dwell time in the adiabatic transfer line that goes from the output of the radiation zone of the furnace to a quenching exchanger and, if necessary, the dwell time in the input cone of this exchanger.

The steam-cracking process according to this invention can preferably be applied in the case where the feedstock comprises at least 20% by weight of ethane, whereby the conversion of the ethane of the feedstock is greater than or equal to 77%, or a conversion CONV$\geq$77.

If the feedstock does not consist of pure ethane, the residual ethane does not reflect exactly the unconverted fraction of the ethane of the feedstock. Actually, when a feedstock that also comprises other hydrocarbons is cracked, these hydrocarbons provide during their cracking significant amounts of ethane which are added to the ethane initially contained in the feedstock. Thus, if the residual ethane represents 20% or 13% of the initial ethane, the initial ethane conversion was greater than 80% (or 87%).

Typically, for the implementation of this invention, a tubular steam-cracking furnace that comprises at least one pipe or coil in the radiation zone whose materials are basically metal alloys is used. The boundary temperature of the materials of the end portion of the pipe is preferably greater than or equal to 1060° C., in particular 1100° C., and in particular greater than or equal to 1120° C., for example between 1120 and 1220° C.

Conventionally, the end portion of the pipe is the downstream portion of the pipe that corresponds to 25% of total length L. Conventionally, boundary temperature $T_L$ of a pyrolysis tube material is the maximum temperature that can be reached by this tube (skin temperature) at the end of the cycle before triggering a decoking procedure. This maximum acceptable temperature is therefore dependent, within a limited range, on the selection of the manufacturer that operates the steam-cracking device, which can use a relatively low value of $T_L$ to favor the service life of the tubes or a higher value to increase the cycle time or the conversion. The recommended values are indicated in Reference 2.

A process is proposed in particular in which:

$20 \leq \emptyset^* \leq 79$, in particular $25 \leq \emptyset^* \leq 70$, more particularly $25 \leq \emptyset^* \leq 64$, in particular $28 \leq \emptyset^* \leq 59$, and, for example, $30 \leq \emptyset^* \leq 55$.

A pipe or steam-cracking coil typically comprises a number (2, 3, 4, 5 or more) of sections with a different inside diameter that generally increases when going from the upstream direction to the downstream direction. It can also have clusterings of tubes between one another. Conventionally, the ratio of $$R = \frac{L}{D_H}$$

is calculated by adding (by going from the upstream direction to the downstream direction) of the length to inside diameter ratios of each section. If a coil comprises several tubes that operate in parallel with their clustering, it is necessary to take into consideration only one of them, by following a single flow line. By definition, there is then $$D_H = \frac{L}{R}.$$

The ratio of $$R = \frac{L}{D_H}$$

is generally greater than or equal to 560 and less than or equal to 1400, preferably confirming $1400 \geq R \geq 620$, and typically such that $1300 \geq R \geq 670$, in particular $1200 \geq R \geq 700$, in particular $1150 \geq R \geq 740$, and for example $1100 \geq R \geq 770$.

According to the invention, high ratios of pipe length to pipe diameter and low fluxes are usually used. $\emptyset^*$ is a corrected flux to take into account the possible usage either of anti-coking surface deposits or tubes that comprise straight or helicoidal fin that improve the thermal transfer, whereby these techniques make it possible to increase the usable thermal flux. Design parameter $\xi_1$ takes into account both the ratio $R=L/D_H$ and corrected flux $\emptyset^*$.

Without being linked by any theory, it was found that the current limitations of the ethane conversion resulted from two phenomena:

1) Kinetic Aspect:

Let us consider, for example, a recent furnace design that from a conventional point of 650° C. uses a thermal flux of 90 KW/m², a length of coil L that makes it possible to obtain at the furnace outlet a conversion of 65%. If it is desired to increase the conversion to reach 80%, notably the thermal flux will logically be increased beyond 90 KW/m². This will have the result of increasing the conversion, but also the reaction temperatures. In any steam-cracking furnace, there is competition between the heat input, which tends to increase the temperature of the reaction medium, and the kinetics of cracking which tends to cool the reaction medium because of the endothermic reactions of cracking. When it is desired to achieve very high conversion levels such as 77 to 97%, the thermokinetic modelization of the pyrolysis coil makes it possible to analyze that at the end of the reaction zone, a negative factor opposing the cooling of the medium is the significant reduction of the hydrocarbons and the ethane that are not yet cracked. The result is that the output temperature greatly increases without the cooling by cracking being adequate to moderate this temperature increase. This phenomenon is all the more significant as the thermal flux is high. The result is a significant increase of the temperatures of the furnace output and the tube skin, with an accelerated coking, which means that it cannot work on an industrial scale.

If, in contrast and paradoxically, low thermal fluxes are used, lower than those currently employed under industrial conditions, compensated by an increase of the $L/D_H$ ratio, it is possible to reestablish a favorable balance in maintaining acceptable temperatures in the competition between heating and cooling: time is allowed for the reaction to continue, and the skin temperatures remain moderate, which makes it possible to preserve an acceptable coking speed.

Preferably $\xi_1$ is such that $1 \leq \xi_1 \leq 9.5$, for example $1 \leq \xi_1 \leq 8.5$, in particular $1.5 \leq \xi_1 \leq 7$, in particular $1 \leq \xi_1 \leq 6$; the recommended values of $\xi_1$ are such that $1.3 \leq \xi_1 \leq 5.2$ and particularly $1.4 \leq \xi_1 \leq 4.5$.

A process is also presented in which parameter $\xi_2$ is defined by:

$$\xi_2 = \frac{[\emptyset^*]^2}{R} \times f(CONV) \times g(T_{MT})$$

with $$f(CONV) = 1 + 0.4\sqrt{\frac{CONV - 77}{100}}$$

where CONV is the conversion percentage of the ethane of the feedstock, and $$g(T_{MT}) = 5.07 \times 10^9 e^{\left(\frac{-28000}{T_{MT}+273}\right)}$$

with $T_{MT}$ (° C.)=maximum temperature of the skin of the tubes at the beginning of the cycle in the portion of the radiation zone that corresponds to a dwell time that is greater than or equal to 110 ms,
is such that: $1 \leq \xi_2 \leq 20$, in particular $1 \leq \xi_2 \leq 15$, in particular $1 \leq \xi_2 \leq 13$, in particular $1 \leq \xi_2 \leq 11$ and preferably $1 \leq \xi_2 \leq 9$, whereby flux $\emptyset$ is adequate, but $\xi_2$ is low enough to reach a conversion percentage of the ethane of the feedstock: CONV>77 and to maintain it (to be able to maintain it) at this level for a cycle time of at least 8 days, in particular at least 10 days, in particular at least 15 days, more particularly at least 20 days and typically at least 30 days.

$\xi$ is the parameter of modified design, to take into account the level of conversion, on the one hand, and the maximum temperature of the skin of the tubes on the other hand (observed beyond the initial cracking zone).

A process is also presented in which ratio R is selected, and thermal flux $\emptyset^*$ is adjusted such that parameter $\xi_3$ that is defined by $$\xi_3 = \frac{\Delta T_{OPER}}{\emptyset^* \times f(CONV) \times g(T_{MT})}$$

is such as
$5 \geq \xi_3 \geq 0.25$, and in particular
$4 \geq \xi_3 \geq 0.5$, in particular $4 \geq \xi_3 \geq 0.6$, more particularly
$4 \geq \xi_3 \geq 0.7$, and preferably $3.5 \geq \xi_3 \geq 0.8$,
with $\Delta T_{OPER}=T_L-T_{MT} \geq 30°$ C., where $T_L$ is the boundary operating temperature of the end portion of the pipe results, whereby flux $\emptyset$ is adequate, but $\xi_3$ is large enough to reach a conversion percentage CONV>77 and to maintain it (to be able to maintain it) at this level for at least one cycle time of at least 8 days, in particular at least 10 days, in particular at least 15 days, more particularly at least 20 days and typically at least 30 days.

$\xi_3$ is the operating parameter, whose evolution mainly reflects the cycle time of the furnace. The larger $\xi_3$ is, the higher the cycle time. The expression of $\xi_3$ shows that it is necessary to have a boundary temperature $T_L$ that is significantly greater than the maximum skin temperature at the beginning of the cycle (to allow the coking to take place and to increase the skin temperature during a high cycle time). It is also necessary to have a relatively low skin temperature $T_{MT}$ so that correcting coefficient $g(T_{MT})$ is the smallest possible (whereby this coefficient reflects a coking speed index, linked to the skin temperature).

Length L of the pipe can be defined by the equation:

$$L \geq K \times \frac{Q \times \Delta H_{70}}{\emptyset S_L} \text{ with}$$

$2 \geq K \geq 1.05$, and in particular $1.6 \geq K \geq 1.1$ where:
Q is the mass flow rate of the feedstock that is diluted with water vapor, Kg/s, $\Delta H_{70}$ is the transferred heat that corresponds to a conversion of 70% of the ethane, Kj/Kg, $S_L$ is the mean linear outside surface of the pipe in the heating zone: $m^2/m$.

Dwell time τ is advantageously such that:
250 ms≦τ≦1500 ms, more particularly 350 ms≦τ≦1200 ms, in particular 350 ms≧τ≧100 ms, and typically 400 ms≦τ≦950 ms.

If ppHC (bar absolute) is used to represent the partial pressure of hydrocarbons+hydrogen in the effluents, in furnace output, then generally: 0.2≦ppHC≦2.8, in particular 0.3≦ppHC≦2.8 and preferably 0.4≦ppHC≦1.6.

The furnace output temperature is typically such that: COT≧876° C., and in particular confirms 980≧COT≧858+10 [f(CONV)+ppHC]

and COT≧876° C.

These values make it possible not to come too close to the values of the ethane/ethylene equilibrium (whereby COT is greater than the equilibrium temperature). When work is done at a very high conversion level, for example CONV≧90, it is preferable to use COT temperatures ≧910° C.

According to a variant of the process, the effluents of the radiation zone can pass through an approximately adiabatic zone with a dwell time τ* such that: 1 ms≦τ*≦220 ms, and in particular 8 ms≦τ*≦80 ms, before their input into a quenching zone (ms=milliseconds).

The maximum temperature of the tubes' skin at the beginning of the cycle is generally kept at a moderate value, generally: 975° C.≦$T_{MT}$≦1060° C, and in particular 980° C.≦$T_{MT}$≦1050° C. and in particular 990° C.≦$T_{MT}$≦1044° C., and preferably 1000° C.≦$T_{MT}$≦1038° C.

The sizing parameters of the furnace will preferably be selected so as to have:

50° C.≦$T_{MT}$-COT≦130° C., and in particular:

80° C.≦$T_{MT}$-COT≦106° C.

According to a characteristic variant of the process, the end portion of the pipe can comprise at least one tubular element of the group that is formed by the pyrolysis tubes with an anti-coking inside coating and pyrolysis tubes that comprise an approximately helicoidal inside fin. This makes it possible to lower the maximum skin temperature $T_{MT}$ and to increase the cycle time.

Typically, the feedstock can circulate in pyrolysis tubes whose inside diameters are between:
45 and 180 mm, in particular between 65 and 130 mm.

Typically, dilution rate d of the feedstock by the water vapor (fraction by weight of water vapor/hydrocarbon feedstock) is such that 0.05≦d≦2, in particular 0.15≦d≦1 and preferably 0.2≦d≦0.8.

The cycle time is typically at least 15 days, in particular at least 20 days and preferably greater than or equal to 30 days.

The conversion of ethane is generally selected so that the residual ethane that is contained in the effluents of the quenching zone is less than or equal to 24% by weight, in particular 15% by weight, of the ethane that is contained in the feedstock. Typically, the conversion of the ethane of the feedstock is greater than or equal to 85%, in particular CONV≧88, in particular CONV≧90. If the feedstock contains propane, a conversion of the propane of the feedstock that is greater than or equal to 97%, in particular 98%, will preferably be selected.

The invention also proposes, for the execution of the process, a steam-cracking furnace under very severe conditions that comprises a convection zone for the preheating of a hydrocarbon feedstock that comprises at least 20% by weight of hydrocarbons with 2 or 3 carbon atoms, diluted with water vapor, a radiation zone that is connected upstream from the convection zone and downstream from a quenching zone, whereby the radiation zone comprises a number of pipes of ratio $$\frac{L}{D_H}$$

that is greater than or equal to 680 and heating means of the feedstock that is diluted with water vapor at a temperature of at least 876° C.

Typically, it is possible to have:

$$2000 \geq \frac{L}{D_H} \geq 700,$$

in particular:

$$2000 \geq \frac{L}{D_H} \geq 760.$$

The furnace comprises in particular heating means that deliver to said pipes a nominal flux ø that confirms 20 KW/$m^2$≦ø≦79 KW/$m^2$, and in particular 25 KW/$m^2$≦ø≦64 KW/$m^2$.

The end portion of the pipes typically has a boundary operating temperature $T_L$≧1100° C., in particular 1220° C.≧$T_L$≧1120° C.

The invention will be better understood following the description of the referenced figures, where:

Figure 1:
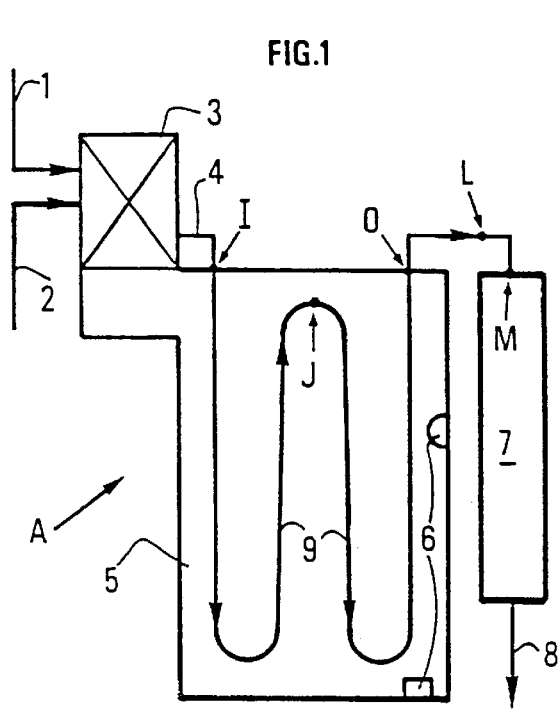
FIG. 1 represents a conventional tubular steam-cracking furnace for the cracking of ethane at 65%, not according to the invention.

In FIG. 1, a hydrocarbon feedstock that is high in ethane falls in 1 into a convection zone 3 of furnace A. In this zone, a supply of water vapor 2 makes it possible, after mixing with the hydrocarbon feedstock, to obtain a mixed feedstock that is preheated between 600 and 700° C., typically at 650° C., then leaves the convection zone via a pipe 4 and reenters at point 1 in a radiation zone 5 that comprises burners 6 of several types (bottom, side radiant burners). The preheated feedstock circulates in parallel in a number of pipes or coils with pyrolysis tubes 9 (whereby a single coil is shown) and leaves from the radiation zone at point 0. A short transfer line makes it possible to reach point M, which is the inlet of a primary quenching exchanger 7.

In this conventional furnace A (of "W" type), the inside diameter of the pyrolysis tubes varies. The first two vertical pitches of the furnace, between inlet I and point J, consist of tubes (forming a pin) with an inside diameter of 80 mm and a thickness of 8 mm (96 mm outside). The next two pitches consist of tubes with an inside diameter of 105 mm and a thickness of 8 mm, forming a second pin between point J and the outlet of the furnace at point O. The length of first pin IJ is 25 m, just like that of second pin JO. The ratio of $$R = \frac{L}{D_H}$$

is therefore equal to the sum of the length/inside diameter ratios of each of the pins or:

$$\frac{25}{0.08} + \frac{25}{0.105} = 550.60.$$

Furnace output temperature COT is measured between 0 and M, preferably at point L, located in the middle of short transfer line OM (for example, with a length of 3 m).

At the outlet of primary quenching exchanger 7, of double-tube type, the effluents are sent via a pipe 8 to a secondary quenching exchanger, not shown, and downstream units for treating and fractionating cracked gases.

The operation of this furnace was simulated in a steam-cracking furnace model with the following results:

During nominal operation, whose main conditions are summarized in first column A1 of Table 1, 1500 Kg/h of ethane is fed into each coil, under an input pressure of 2.3 bar absolute, with a dilution rate of d=0.3 (or 450 Kg/h) of diluted water vapor). In practice, small amounts of sulfur-containing products are also injected with the feedstock (for example, several tens of ppm by weight of sulfur, relative to the ethane feedstock, in the form of DMDS: dimethyl disulfide) to reduce the catalytic coking.

The mixed feedstock is preheated to 650° C. and returns to J in the radiation. zone. In this zone (5), thermal flux ø that is transmitted to the tubes is about 71.6 KW per m² of outside surface. The results of this simulation provide an ethane conversion of 64% with a furnace output temperature of 865° C. and a maximum skin temperature at the beginning of the cycle (non-coked pyrolysis coil) of 1014° C. Typically, the second pin is in HP mode, which allows a boundary temperature $T_L$ at the end of the cycle of 1125° C.

Under these conditions of temperatures, flux and skin temperatures, the coking is not considerable, and the industrial operation is possible with cycle times that notably exceed 15 days. A specific cycle time cannot be calculated, because it depends on a very large number of factors such as the exact nature of the alloy, the inside surface state of the tubes, the age of the tubes and the chronology of past operating conditions, the arrangement of the burners and the shape of the vertical profile of thermal flux, etc. . . .

This furnace is therefore able to operate in a satisfactory manner at about 65% of the conversion of ethane.

If reference is now made to second column A2 of Table 1, then to columns A3 and A4, it is possible to observe the consequences, for this same furnace A, and the same feedstock, of an operation with an increased level of severity and conversion.

The conversion is thus brought to 75%, then 81%, then 90% by increase of the thermal flux, which passes from 71.6 KW/m² to 82 then 88 then 98.3 KW/m² of the outside surface.

In the same step, a significant increase of the furnace output temperatures (COT) and especially the maximum skin temperatures of tubes $T_{MT}$ can be noted. At 75% conversion, this temperature is established at 1045° C. This value is high and corresponds to a significant coking speed. This coking speed could be accepted if the thermal flux were very low, for example on the order of 30 to 35 KW/m²:

There would then be a significant daily increase of the coke thickness, but a daily increase of the skin temperature of the tubes would remain acceptable because of a low thermal flux: the daily temperature increase is actually proportional to the thermal flux.

In contrast, furnace A, with a flux of 82 KW/m² and a skin temperature $T_{MT}$ of 1045° C., has a daily increase of high temperature and a very short cycle time that is not very compatible with industrial operation. This is also further aggravated especially when the conversion is pushed beyond 75%.

Figure 2:
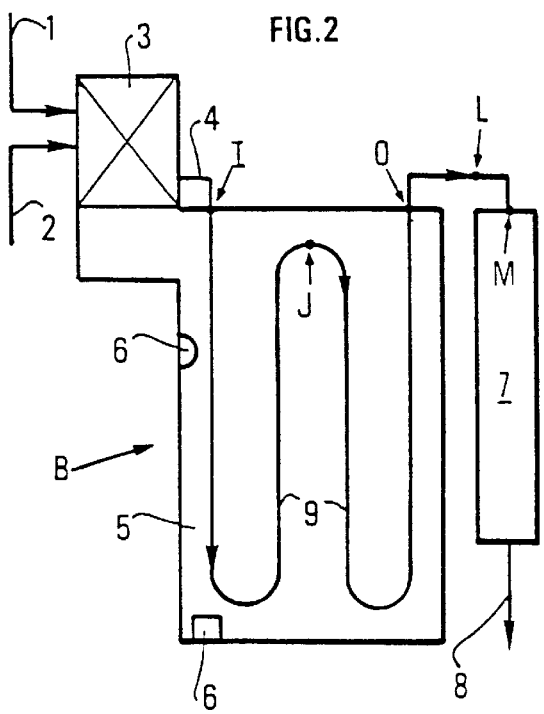
FIG. 2 represents a tubular steam-cracking furnace for the implementation of the process according to the invention.

FIG. 2 represents an unconventional steam-cracking furnace B, according to the invention, because of the dimensional characteristics and operating parameters that are not indicated in the figure but are explained below: thus furnace B of FIG. 2 comprises a coil of pyrolysis tubes 9 of which the upstream portion (2 first pins) is identical to that of furnace A, i.e., 25 m of tubes with an inside diameter of 80 mm and 25 m of tubes with an inside diameter of 105 mm. In contrast, this coil is extended by another pin of 25 m of tubes with an inside diameter of 105 mm. The coil therefore has a total length of 25+50=75 m and a ratio of $$R = \frac{L}{DH} = \sum \frac{Li}{Di},$$

increased in particular relative to furnace A: (Li/Di represents the length/inside diameter ratio of the i'th pitch or i'th vertical line length of circulation of the feedstock in the radiation zone of the furnace), thus, $$R = \frac{25}{0.08} + \frac{50}{0.105} = 788.7$$

(whereby the pitches have been grouped in sections with the same diameter).

A second difference relative to furnace A relates to the thermal flux, which is greatly decreased; in addition, the feedstock flow rate is decreased relative to that of furnace A. Finally, the dwell time was increased. If reference is made to Table 1, the two cases of operation of furnace B are indicated in columns 5 and 6 (cases B1 and B2).

First case of operation B1 makes it possible to reach a conversion of 83.4% with a thermal flux of ø=53.8 KW, and a maximum skin temperature $T_{MT}$ of 1000° C. at the beginning of the cycle.

These conditions are moderate and make it possible to operate with a high cycle time, typically greater than 1 month. This cycle time is high for three reasons: On the one hand, the maximum skin temperature of tubes $T_{MT}$ is relatively low, which leads to a relatively moderate coking speed (in mm per month of coke).

On the other hand, this relatively low temperature makes possible a relatively high temperature increase, before reaching boundary operating temperature $T_1$: this available operating ΔT (ΔToper) is high.

Finally, whereby thermal flux ø is relatively low, the increase of skin temperature of the tubes that corresponds to a given coke thickness e is relatively low. Actually, the ΔT that is due to the coke is written as:

$$\Delta T = \frac{\emptyset \times e}{\lambda}.$$

If ø is low, ΔT is limited. The furnace according to the invention therefore makes it possible to reach a high ethane conversion of 83.4% without operating problems, with a cycle time as long as that of a conventional furnace.

In the case of operation B2, a low thermal flux (51 KW/m²) is preserved, and the feedstock flow rate is reduced to reach an ethane conversion of 92%. Under these conditions, the furnace output temperature is 918° C., and the maximum skin temperature of the tubes at the beginning of the cycle is 1018° C. This mean value is acceptable as well because of the moderate value of the thermal flux. The cycle time of this furnace, at 92% of ethane conversion, is typically greater than 20 days.

To increase this cycle time, it would be possible to act on various parameters: to increase the $L/D_H$ ratio, for example by using pins of 27 m instead of 25 m; as an alternative, the feedstock flow rate and flux ø could be reduced, or then the performances of the materials of the tubes of the end portion (25% of the length) of the coil could be increased by using alloys of 35/45 type or with 40% chromium and more, having a boundary temperature of 1150° C. or higher still. Tubes that have a helicoidal inside fin that increases the thermal transfer or that have an anti-coking inside coating (for example multilayers of "CoatAlloy" type presented in Reference 4) could also be used in the end portion.

Figure 3:
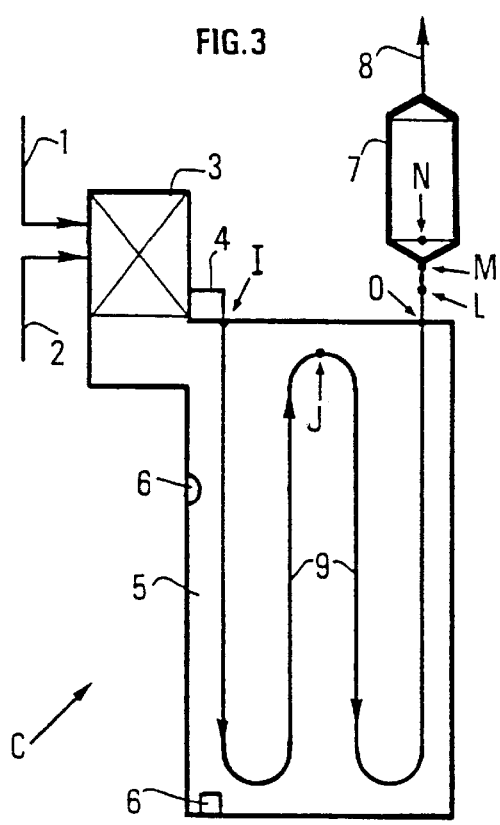
FIG. 3 represents another tubular steam-cracking furnace for the implementation of the process according to the invention.

Reference is now made to FIG. 3, which represents another type of furnace C, according to the invention, by its dimensional characteristics and operating parameters.

This furnace comprises a number of coils comprising tubes with inside diameters that are relatively larger than those of the tubes of furnaces A and B. Each coil, one of which is shown in FIG. 3, comprises 10 vertical pitches of circulation (i.e., 5 pins).

The first two pins are produced with tubes with an inside diameter of 115 mm, a thickness of 8 mm, and with a total length of 50 m (for the two pins).

The other three pins are produced with tubes with an inside diameter of 150 mm and a thickness of 8 mm, and with a total length of 75 m. Ratio $$R = \frac{L}{D_H}$$

of this coil is therefore equal to:

$$R = \frac{50}{0.115} + \frac{75}{0.150} = 934.8.$$

Mean hydraulic diameter $D_H$ is therefore such that $$D_H = \frac{L}{R} = \frac{50+75}{934.8} = 133.7 \text{ mm}.$$

In operating mode C1 whose conditions are provided in Table 1, 2800 kg/h of ethane is supplied to furnace C in the coil described above under 2.3 bar absolute and is cracked in the presence of water vapor with a conversion of 82.7%. Maximum skin temperature $T_{MT}$ is moderate: 978° C. and thermal flux ø is low: 47 kw/m². Under these conditions, the cycle time is very long and exceeds in particular 1 month.

In the $C_2$ operation, a slightly shorter flow rate of ethane is supplied to each coil of furnace C, with a thermal flux that is approximately identical to that of operation $C_1$. The conversion is established at 92.8% with a maximum skin temperature at the beginning of the cycle $T_{MI}$=1005° C. Under these conditions, the cycle time is in particular greater than 20 days and typically greater than or equal to one month. Furnace C according to the invention therefore makes it possible to operate with satisfactory industrial conditions and with an ethane conversion that can exceed 92%.

The feedstock losses at the beginning of the cycle of furnaces B and C vary between 0.5 and 0.75 bar approximately and remain moderate.

Parameters $\xi_1$, $\xi_2$ and $\xi_3$ of furnaces B and C according to the invention are very different from those of furnace A, regardless of the level of severity and the conversion obtained.

The invention therefore makes it possible, by using values of these parameters within the range of values of Examples B and C, to design and to optimize a steam-cracking furnace or at least to obtain a very satisfactory operation that is perfectly compatible with the industrial requirements for very high ethane conversions such as 77% to 92% and more.

The higher the desired conversion, the more important it is to use a high ratio of length to diameter $$\frac{L}{D_H},$$

as well as a moderate thermal flux. Furnace C thus has longer cycle times than furnace B.

A more specific evaluation of the cycle time based on the conversion can be obtained, if necessary, thanks to a pilot furnace with a very high $$\frac{L}{D_H}$$

ratio (for example 1200), and with such a furnace, it is possible to evaluate, over a short period, the coking speed based on the conversion, at a constant skin temperature $T_{MT}$, and also the influence of the skin temperature on the coking speed with constant conversion.

The coking speeds that are obtained preferably will not be used for the evaluation of the cycle time of an industrial furnace. In contrast, the tendencies of evolution (corrective factors) that make it possible to take into account parameters of conversion (CONV) and maximum skin temperature ($T_{MT}$) can be used starting from the known experimental values of the coking speed of a given furnace with a conventional degree of severity of 65%.

During the operation of an industrial furnace, the operating conditions should be adjusted relative to the calculated values to obtain the desired conversion. This can be done by analyzing the cracked gases, for example by chromatography, by measuring the conversion and by modifying the thermal flux and/or the feedstock flux rate to be adjusted to the desired conversion.

The invention makes it possible to provide rules for the design of furnaces and for the increase of cycle times that make it possible to operate with very high ethane and/or propane conversions such as 77 to 97% of ethane conversion, values that are considered as being incompatible with an industrial operation with tubular furnaces with tubes made of metal alloys in the current state of the art.

The use of these furnaces makes it possible to reduce the reserve of unconverted ethane and to debottleneck a steam-cracking device, in particular the sections for compression of cracked gases and fractionation.

The use of these furnaces also makes it possible to obtain in the effluents a very low ethane (unconverted) to total C2 fraction (mainly ethane+ethylene) ratio. Under these conditions, fraction C2, after selective hydrogenation (alone or mixed with the C3 fraction, or mixed in the recompressed cracked gases) to eliminate the acetylene compounds, can be used in petrochemical processes that use ethylene (for example production of polyethylene) without preliminary ethane/ethylene fractionation.

It is possible to use the following stages:

1) Steam-cracking of a main feedstock (standard and/or according to the invention)+steam-cracking of recycled ethane according to the invention.

2) Selective hydrogenation of the C2 fraction by itself or in a mixture.

3) Ethylene conversion process (for example production of polyethylene) that is supplied by the crude C2 fraction, without ethane/ethylene fractionation, then recycling of unconverted ethane in the steam-cracking device (stage 1).

Whether for increasing the conversion, debottling a steam-cracking device, or for being able to use an unfractionated crude C2 fraction in a downstream conversion process, the process according to the invention makes it possible to reach, in a simple and reliable way, conversion levels of ethane (and/or propane) that are considered as inaccessible in the state of the art of the tubular furnaces with metal pyrolysis tubes.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 99/06.190, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A steam-cracking process comprising a feedstock that contains at least 80% by weight of hydrocarbons that have 2 to 4 carbon atoms, and at least 20% by weight of hydrocarbons selected from the group consisting of ethane and propane, that is diluted with water vapor in a radiation zone of a furnace and is circulated in at least one pipe having a length $L \geq 16$ m and a hydraulic diameter that is greater than or equal to 34 mm in the end portion of the pipe, under the following conditions of dwell time $\tau$ and furnace output temperature COT:

$$150 \text{ ms} \leq \tau \leq 2800 \text{ ms};$$

$$858° \text{ C.} \leq \text{COT} \leq 1025° \text{ C.},$$

wherein the ratio of L/mean hydraulic diameter $D_H$, and dwell time $\tau$ are large enough to obtain at least one of the following results:
a conversion of at least 77% of the ethane of the feedstock, if the feedstock contains ethane,
a conversion of at least 96% of the propane of the feedstock, if the feedstock contains propane,

TABLE 1

| TYPE OF FURNACE | A1 | A2 | A3 | A4 | B1 | B2 | C1 | C2 |
|---|---|---|---|---|---|---|---|---|
| FURNACE OUTPUT TEMPERATURE COT (° C.) | 865 | 884 | 909 | 940 | 897 | 918 | 886 | 916 |
| DWELL TIME $\tau$ (MS) | 322 | 310 | 304 | 292 | 509 | 608 | 808 | 915 |
| ETHANE FLOW RATE Kg/H | 1500 | 1500 | 1500 | 1500 | 1400 | 1200 | 2800 | 2500 |
| DILUTION RATE d Kg/Kg | 0.3 | 0.3 | 0.3 | 0.3 | 0.3 | 0.3 | 0.3 | 0.3 |
| RADIATION INPUT TEMPERATURE (° C.) | 650 | 650 | 650 | 650 | 650 | 650 | 650 | 650 |
| MAXIMUM SKIN TEMPERATURE (BEGINNING OF CYCLE) TMT (° C.) | 1014 | 1045 | 1068 | 1106 | 1000 | 1018 | 978 | 1005 |
| END PORTION BOUNDARY TEMPERATURE TL (° C.) | 1125 | 1125 | 1125 | 1125 | 1125 | 1125 | 1125 | 1125 |
| INSIDE DIAMETERS (mm) | 80/105 | 80/105 | 80/105 | 80/105 | 80/105 | 80/105 | 115/150 | 115/150 |
| RATIO R = L/DH | 550.60 | 550.60 | 550.60 | 550.6 | 788.7 | 788.7 | 934.8 | 934.8 |
| $\xi_1$ | 9.31 | 12.2 | 14.06 | 17.50 | 3.67 | 3.30 | 2.36 | 2.37 |
| $\xi_2$ | not def. | not def. | 65.93 | 154.35 | 5.74 | 7.36 | 2.49 | 4.25 |
| $\xi_3$ | not def. | not def. | 0.138 | 0.0219 | 1.485 | 0.941 | 2.96 | 1.419 |
| ETHANE CONVERSION CONV (%) | 64 | 75.3 | 81.2 | 90 | 83.4 | 92 | 82.7 | 92.8 |
| 526 (KW/M2) | 71.6 | 82 | 88 | 98.3 | 63.8 | 51 | 47 | 47.1 | wherein thermal flux ø in the radiation zone is low enough so that parameter $\xi_1$, that is defined by:

$$\xi_1 = \frac{[\varnothing^*]^2}{R}$$

with:

$R = L/D_H$, $\varnothing^* = \varnothing \times F$ where ø is the mean thermal flux that is sent into the pipe in the radiation zone, in KW per m² of outside surface of the pipe, and F=
0.85 if the end portion of the pipe comprises at least one inside fin or an anti-coking coating on at least one portion of its inside surface,
0.72 if the end portion of the pipe comprises at least one inside fin and an anti-coking coating on at least one portion of its inside surface, and
1 otherwise,
has a value of $\xi_1 \leq 11$ and is low enough to maintain this conversion for a cycle time that is greater than or equal to about 8 days.

2. A process according to claim 1, wherein the feedstock comprises at least 20% by weight of ethane, whereby the conversion of the ethane of the feedstock is greater than or equal to 77%.

3. A process for steam-cracking according to claim 1, in a tubular furnace that comprises in the radiation zone at least one pipe, in which the boundary temperature of the materials at the end portion of the pipe is greater than or equal to 1060° C.

4. A process according to claim 1, wherein:

$20 \leq \varnothing^* \leq 79$.

5. A process according to claim 1, wherein the ratio of $$R = \frac{L}{D_H}$$

is greater than or equal to 560 and less than or equal to 1400.

6. A process according to claim 1, wherein $\xi_1$ is:

$1 < \xi_1 \leq 8.5$.

7. A process according to claim 2, wherein parameter $\xi_2$ that is defined by:

$$\xi_2 = \frac{[\varnothing^*]^2}{R} \times f(CONV) \times g(T_{MT})$$

with F(CONV)=1+0.4

$$f(CONV) = 1 + 0.4 \sqrt{\frac{CONV - 77}{100}}$$

where CONV is the conversion percentage of the ethane of the feedstock, and $g(T_{MT}) = 5.07 \times 10^9 e^{\left(\frac{-28000}{T_{MT}+273}\right)}$ with $T_{MT}$ (°C.)=maximum temperature of the skin of the tubes at the beginning of the cycle in the portion of the radiation zone that corresponds to a dwell time that is greater than or equal to 110 ms, is:

$1 \leq \xi_2 \leq 20$, and $\xi_2$ is low enough to reach a conversion percentage of the ethane of the feedstock: CONV>77 and to maintain it at this level for a cycle time of at least 8 days.

8. A process according to claim 7, wherein parameter $\xi_3$ that is defined by:

$$\xi_3 = \frac{\Delta T_{OPER}}{\varnothing^* \times f(CONV) \times g(T_{MT})} \text{ is}$$

$5 \geq \xi_3 \geq 0.25$, with $\Delta T_{OPER} = T_L - T_{MT} \geq 30°$ C., where $T_L$ is the boundary operating temperature of the end portion of the pipe, and wherein $\xi_3$ is large enough to reach a conversion percentage CONV>77 and to maintain it at this level for at least one cycle time of at least 8 days.

9. A process according to claim 2, wherein the length of pipe L is defined by the equation:

$$L \geq K \times \frac{Q \times \Delta H_{70}}{\varnothing S_L} \text{ with}$$

$2 \geq K \geq 1.05$ where:
Q: the mass flow rate of the feedstock that is diluted with water vapor, Kg/s,
$\Delta H_{70}$: the transferred heat that corresponds to a conversion of 70% of the ethane, Kj/Kg,
$S_L$: the mean linear outside surface of the pipe in the heating zone: m²/m.

10. A process according to claim 1, wherein dwell time τ is 250 ms $\leq \tau \leq$ 1500 ms.

11. A process according to claim 1, wherein:

$0.2 \leq ppHC \leq 2.8$, with ppHC (bar absolute)=partial pressure of hydrocarbons+hydrogen in the furnace output effluents.

12. A process according to claim 11, wherein:

876° C. $\leq$ COT $\leq$ 1025° C.

13. A process according to claim 1, further comprising traversing the effluents of the radiation zone through an approximately adiabatic zone with a dwell time τ*, wherein 1 ms $\leq \tau^* \leq$ 220 ms, and further sending the effluents into a quenching zone.

14. A process according to claim 7, wherein the maximum skin temperature of the tubes at the beginning of the cycle is maintained at 975° C. $\leq T_{MT} \leq$ 1060° C.

15. A process according to claim 7, wherein $$50°\,C. \leq T_{MT}-COT \leq 130°\,C.$$

16. A process according to claim 1, wherein the end portion of the pipe comprises at least one tubular element with an inside anti-coking coating and an inside fin.

17. A process according to claim 1, wherein the cycle time is greater than or equal to 15 days.

18. A process according to claim 1, wherein dilution rate d of the feedstock by the water vapor, fraction by weight, is:

$$0.05 \leq d \leq 2.$$

19. A process according to claim 13, wherein effluents from the quenching zone contain ethane in an amount less than or equal to 24% by weight of the ethane that is contained in the feedstock.

20. A process according to claim 1, wherein the conversion of the ethane of the feedstock is greater than or equal to 85%.

21. A process according to claim 1, wherein the conversion of the propane of the feedstock is greater than or equal to 97%.

22. A process according to claim 3, wherein said boundary temperature is between 1120 and 1220° C.

23. A process according to claim 4, wherein:

$$25 \leq \phi^* \leq 64.$$

24. A process according to claim 5, wherein:

$$1300 \geq R \geq 670.$$

25. A process according to claim 6, wherein:

$$1.5 \leq \xi_1 \leq 7.$$

26. A process according to claim 7, wherein:

$$1.5 \leq \xi_2 \leq 17.$$

27. A process according to claim 9, wherein:

$$1.6 \geq K \geq 1.1.$$

28. A process according to claim 10, wherein:

$$350\,ms \leq \tau \leq 1200\,ms.$$

29. A process according to claim 11, wherein:

$$0.4 \leq ppHC \leq 1.6.$$

30. A process according to claim 12, wherein:

$$980 \geq COT \geq 858 + 10[F(CONV)+ppHC].$$

31. A process according to claim 13, wherein:

$$8\,ms \leq \tau^* 80\,ms.$$

32. A process according to claim 14, wherein said value is:

$$990°\,C. \leq T_{MT} \leq 1044°\,C.$$

33. A process according to claim 15, wherein:

$$80°\,C. \leq T_{MT}-COT \leq 106°\,C.$$

34. A process according to claim 17, wherein the cycle time is greater than or equal to 30 days.

35. A process according to claim 18, wherein:

$$0.15 \leq d \leq 1.$$

36. A process according to claim 19, wherein the residual ethane, contained in the effluents of the quenching zone, is less than or equal to 15% by weight, of the ethane that is contained in the feedstock.

37. A process according to claim 20, wherein:

$$CONV \geq 88.$$

38. A process according to claim 20, wherein:

$$CONV \geq 90.$$

39. A process according to claim 21, wherein the conversion of the propane of feedstock is greater than or equal to 98%.

* * * * *

UNITED STATES PATENT AND TRADEMARK OFFICE
CERTIFICATE OF CORRECTION

PATENT NO. : 6,488,839 B1
DATED : December 3, 2002
INVENTOR(S) : Eric Lenglet et al.

It is certified that error appears in the above-identified patent and that said Letters Patent is hereby corrected as shown below:

Column 18,
Line 7, reads "$_{pp}HC$," should read -- $_{pp}HC$ and $COT \geq 876°C$ --.
Line 11, reads "$8_{ms} \leq T*80_{ms}$," should read -- $8_{ms} \leq \tau* \leq 80_{ms}$ --.

Signed and Sealed this

Eighteenth Day of May, 2004

JON W. DUDAS
*Acting Director of the United States Patent and Trademark Office*